United States Patent
Slocum et al.

(10) Patent No.: US 8,867,037 B2
(45) Date of Patent: Oct. 21, 2014

(54) APPARATUS AND METHOD FOR DETECTING GLYCOL

(71) Applicant: Robert Bosch GmbH, Stuttgart (DE)

(72) Inventors: Alexander H. Slocum, Bow, NH (US); Melanie Margarete Hoehl, Cambridge, MA (US); Peter James Lu, Cambridge, MA (US)

(73) Assignee: Robert Bosch GmbH, Stuttgart (DE)

( * ) Notice: Subject to any disclaimer, the term of this patent is extended or adjusted under 35 U.S.C. 154(b) by 13 days.

(21) Appl. No.: 13/766,269

(22) Filed: Feb. 13, 2013

(65) Prior Publication Data

US 2013/0157350 A1 Jun. 20, 2013

Related U.S. Application Data

(63) Continuation of application No. 12/618,343, filed on Nov. 13, 2009, now abandoned.

(60) Provisional application No. 61/199,289, filed on Nov. 14, 2008.

(51) Int. Cl.
*G01N 21/00* (2006.01)
(52) U.S. Cl.
USPC .......................................................... 356/432
(58) Field of Classification Search
USPC .......................................................... 356/342
See application file for complete search history.

(56) References Cited

U.S. PATENT DOCUMENTS

| | | | | | |
|---|---|---|---|---|---|
| 3,918,812 | A | * | 11/1975 | Holm | 356/73 |
| 4,573,796 | A | * | 3/1986 | Martin et al. | 356/318 |
| 5,173,749 | A | * | 12/1992 | Tell et al. | 356/437 |
| 5,930,000 | A | * | 7/1999 | Brand | 356/437 |
| 6,853,452 | B1 | * | 2/2005 | Laufer | 356/436 |
| 6,870,165 | B2 | * | 3/2005 | Amirkhanian et al. | 250/458.1 |
| 7,041,493 | B2 | * | 5/2006 | Rao | 435/288.1 |
| 7,106,442 | B2 | * | 9/2006 | Silcott et al. | 356/338 |
| 7,190,450 | B2 | * | 3/2007 | Chang et al. | 356/318 |
| 7,884,937 | B2 | * | 2/2011 | Prasad et al. | 356/437 |
| 2007/0086006 | A1 | * | 4/2007 | Ebersole et al. | 356/319 |
| 2008/0174768 | A1 | * | 7/2008 | Belz | 356/73 |

FOREIGN PATENT DOCUMENTS

WO PCT/US2009/064402 7/2010

OTHER PUBLICATIONS

U.S. Appl. No. 12/618,343, filed Nov. 13, 2009, Abandoned.

* cited by examiner

*Primary Examiner* — Tarifur Chowdhury
*Assistant Examiner* — Isiaka Akanbi
(74) *Attorney, Agent, or Firm* — Finch & Maloney PLLC

(57) ABSTRACT

A method and apparatus are provided for detecting contaminants, such as ethylene glycol and diethylene glycol, in various materials, including household products, and medicines. The contaminants can be detected using enzyme assays that produce measurable changes in light absorption and/or light fluorescence.

5 Claims, 13 Drawing Sheets

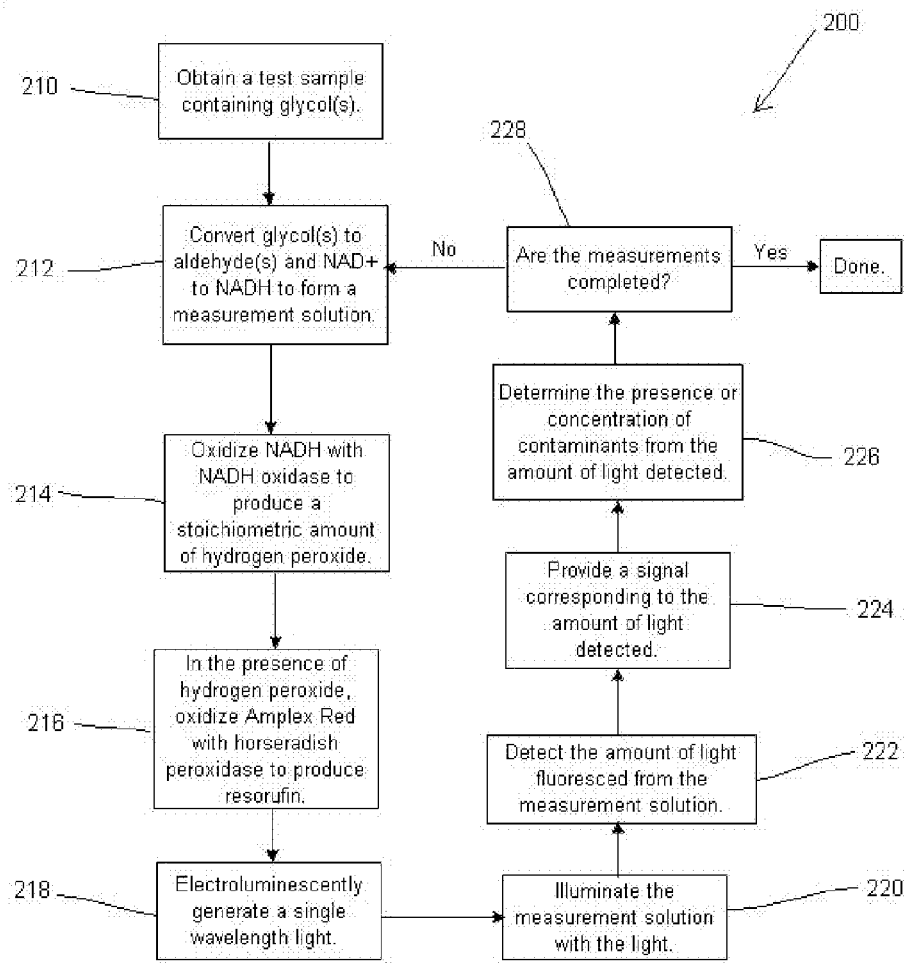

APPARATUS AND METHOD FOR DETECTING GLYCOL

RELATED APPLICATIONS

This application is a continuation of U.S. patent application Ser. No. 12/618,343, filed Nov. 13, 2009, which claims priority to U.S. provisional application Ser. No. 61/199,289 filed on Nov. 14, 2008, the contents of each which are hereby incorporated by reference herein.

STATEMENT REGARDING FEDERALLY SPONSORED RESEARCH

This invention was made in part with government support under an award from CIMIT, whose parent award is from the Department of Defense U.S. Army Medical Research and Material Command. The cooperative agreement number is W81XWH-07-2-0011. The Government may have certain rights in the invention.

BACKGROUND

1. Field of Invention

This invention relates to a method and apparatus for detecting contaminants and specifically to a method and apparatus for providing an assay for detecting glycols in consumer products.

2. Discussion of Related Art

Contamination of various products and materials can cause serious injuries to people and property. For example, contamination of common household products and medicines by poisons such as ethylene glycol (EG) and diethylene glycol (DEG) has killed thousands worldwide in recent years. In addition, contamination of process materials, such as the boiler and feed water used in nuclear reactors can cause corrosion and premature failure of expensive machinery. It is therefore desirable to be able to detect contaminants, such as EG and DEG, in various materials before they can cause harm.

SUMMARY

The invention provides a method and apparatus for determining the presence of and/or amount of one or more contaminants in a test sample.

In one embodiment, a method of detecting at least one of ethylene glycol and diethylene glycol in a sample is provided that includes reacting a glycol with NAD+ in the presence of an alcohol dehydrogenase to produce NADH, oxidizing NADH with an oxidase to produce hydrogen peroxide, oxidizing a fluorogenic substrate in the presence of the hydrogen peroxide and a peroxidase to convert the dye to a fluorescent form, irradiating the sample at first wavelength, detecting light emission at a second wavelength, and providing a signal corresponding to the amount of light detected.

In another embodiment, a method of detecting ethylene glycol and diethylene glycol is provided that includes reacting the sample with a coenzyme in the presence of an alcohol dehydrogenase to form a measurement solution, electroluminescently generating a single wavelength ultraviolet light, illuminating the measurement solution with the single wavelength ultraviolet light, detecting ultraviolet light transmitted through the measurement solution, and producing a signal corresponding to the amount of light detected.

In another embodiment, a device is provided comprising at least one cuvette space, each cuvette space comprising a single wavelength light source constructed and arranged to illuminate at least a portion of the cuvette space, a second light source at a wavelength different from the first, the second light source constructed and arranged to illuminate at least a portion of the cuvette space, a light detector positioned to detect light transmitted from the second light source through the cuvette space, and a fluorescence detector positioned to receive light emitted from the cuvette space at a wavelength different than that emitted from either light source.

In another embodiment, a method of detecting a contaminant in a sample is provided that includes intermittently generating an electroluminescent ultraviolet light, intermittently generating an electroluminescent visible light, detecting a quantity of ultraviolet light transmitted through the sample, detecting a quantity of light fluoresced from the sample at a wavelength different than that of the ultraviolet light and the visible light, and determining the concentration of the contaminant using both the amount of light transmitted and the amount of light fluoresced.

The methods and apparatuses disclosed herein may include one or more of a number of different features. For example, any of the following elements could also be implemented into embodiments of the invention: generating an aldehyde; the alcohol dehydrogenase is a yeast alcohol dehydrogenase; oxidizing a fluorogenic substrate includes converting N-acetyl-3,7-dihydroxyphenoxazine (AMPLEX RED®) or AMPLEX ULTRARED® into its fluorescent form; glycol is reacted with the NAD+ in an alkaline environment; glycol is reacted with the NAD+ at a pH of greater than or equal to 7.5; glycol is reacted with the NAD+ at a pH between 7.3 and 9; glycol is reacted with the NAD+ in a Tris-HCl buffer having a pH of about 7.8; glycol is reacted with the NAD+ in a buffer selected from the group consisting of Tris, bicine, Tris Base HCl, bicine NaOH, alkaline pH "Good's," and phosphate buffers; the step of fitting the signal to $V(t)=\beta \exp(t/\tau)+V0$; the step of normalizing a time constant for the sample by a time constant for pure glycol; the signal comprises a voltage signal; normalizing the voltage signal by dividing the voltage signal by a second voltage signal recorded at time equals zero; fitting the normalized voltage signal to $V(t)=1-a^*\exp(b^*t)$; determining an initial slope of the normalized voltage signal, $-dV/dt$, at time equals zero; the device is powered by a portable battery; the device is capable of measuring fluorescence simultaneously in two separate samples; repeating steps one and two at least twice and extinguishing the ultraviolet light prior to generating the visible light and extinguishing the visible light prior to generating the ultraviolet light.

Other advantages, novel features, and objects of the invention will become apparent from the following detailed description of the invention when considered in conjunction with the accompanying drawings. For purposes of clarity, not every component is labeled in the drawings, nor is every component of each embodiment of the invention shown where illustration is not necessary to allow those of ordinary skill in the art to understand the invention.

BRIEF DESCRIPTION OF THE DRAWINGS

FIG. 5 shows a fluorescence method according to one embodiment of the invention.

DETAILED DESCRIPTION

Figure 1:
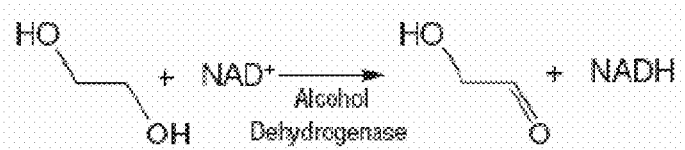
FIG. 1 illustrates an enzyme reaction pathway used in one embodiment of the invention.

Contamination of household and consumer products with poisons such as ethylene glycol (EG) and/or diethylene glycol (DEG) is a lethal public health hazard that episodically kills hundreds to thousands at a time. If not detected and treated promptly, ingestion of even a small amount can result in central nervous system depression, cardiopulmonary compromise, and kidney failure. This contamination has led to several mass-poisonings around the world in the past few decades.

At present there is no simple, specific method to detect the relevant levels of contaminants such as EG and DEG on an industrial scale, particularly in third-world countries that may be most vulnerable to contaminated goods and have the health systems least capable of responding. Standard general test methods, such as gas chromatography or chromatography/mass spectrometry, are expensive, can be slow, have specific power requirements and require specially-trained staff, so they are rarely deployed even in developed countries for identifying contamination in commercial products. Described herein are several devices and procedures that can provide reliable, robust and/or inexpensive tests to detect contaminants, such as EG and DEG, in a wide range of household and other materials.

"Detect" or "detecting" means to determine the presence or amount of a target compound or class of compounds. For example, "detecting" EG in a sample can mean identifying the presence of EG and/or a threshold level of EG in the sample and/or determining the quantitative amount or concentration of EG present in the sample.

"Single wavelength" means 80% of output falls within a 20 nm range. For example, a "single wavelength" light can have 80% of its output fall between 350 and 370 nm.

"Electroluminescently generating" means generating light with an electroluminescent device such as a light-emitting diode (LED) or a laser.

"Sample" includes any substance that may contain a contaminant and/or a species of interest.

This invention provides methods and devices for detecting one or more contaminants in a substrate. The methods and devices may be based on enzyme assays that produce measurable changes in light absorption and/or light fluorescence according to the concentration of contaminants present. For example, in one aspect, an absorbance method is provided that uses a kinetic assay to produce light absorbance changes that vary with contaminant concentration. The light absorbance changes may be measured using a low-cost, single-wavelength device. In another aspect, a fluorescence method is provided that uses a kinetic assay to produce light fluorescence changes. The light fluorescence changes may be determined using a low-cost, single-wavelength device. Any of these methods and devices may be provided in kit form that includes, for example, a package, any combination of the reagents disclosed herein, sample preparation materials, reaction vessels and/or cuvettes, a detection device and instructions for use. Reagents may be in a stabilized form and may be sealed in capsules or ampoules.

In one set of embodiments, the substrate may be any type of material, including: liquids, gels, sols, suspensions, foams, emulsions, and dispersions. In a further set of embodiments, the substrate may be any type of household product or industrial material. Among household products, the substrate may be, for example, any one or combination of: medicine, food, an alcoholic beverage, a non-alcoholic beverage, lotion, cleaning agent, air freshener, or any other household product that may come in contact with humans or other living things.

In another embodiment, the substrate tested may have any rheology, density, and thermal properties. For example, the substrate may have Newtonian or non-Newtonian rheology. The substrate may also have any specific gravity that is typical of industrial materials and household products. In a typical embodiment, the specific gravity will be about 1.0. Regarding thermal properties, the substrate may be thermally conductive or thermally insulating.

In one embodiment, the contaminants detected may be any compound that includes one or more hydroxyl groups. In another embodiment, the contaminants may be any type or combination of alcohol, glycol, and/or glycerol. In another embodiment, the contaminants may be ethylene glycol and/or diethylene glycol. In another embodiment the contaminants may be ethylene glycol and/or diethylene glycol that may be tested for in the presence of other hydroxylated compounds such as alcohols, glycerol and propylene glycol.

In a further embodiment, the contaminants may be detected in the presence of one or more other hydroxylated compounds that are not contaminants. For example, the substrate may be a beverage containing ethyl alcohol, such as wine, and the contaminant detected may be a glycol, such as ethylene glycol and/or diethylene glycol. In another embodiment the contaminants may be ethylene glycol and/or diethylene glycol that may be tested for in the presence of other glycols such as propylene glycol and glycerol.

The concentration of contaminants detected may range from below FDA limits up to 100 percent contaminant. In one embodiment, ethylene glycol is detected in concentrations ranging from below about 1 weight percent up to about 100 weight percent. In a further embodiment, diethylene glycol is detected in concentrations ranging from below about 3 weight percent up to about 100 weight percent.

In a further aspect, this disclosure provides an enzyme assay for detecting one or more contaminants in a substrate. One class of useful enzymes for the assay is the dehydrogenases. In some embodiments, the enzymes may include alcohol dehydrogenase and/or aldehyde dehydrogenase. For example, the enzymes may include yeast alcohol dehydrogenases such as yeast alcohol dehydrogenase USB 10895.

In an additional embodiment, the enzyme assay may include a coenzyme. The coenzyme may be, but is not limited to, NAD+. For example, the coenzyme may be NADP+.

In one embodiment, the enzyme assay includes one or more buffers. For example, the buffers used may be Tris or bicine buffers. Additionally, the buffers may be Tris Base HCl, bicine NaOH, bicine HCl, one or more of alkaline pH range "Good's buffers," and/or phosphate buffer. The pH of the assay materials may range from about 4.0 to about 10.0. In one set of embodiments, the pH may between about 6.0 and 10.0, between 7.0 and 9.0, between 7.5 and 8.6, or about 7.8.

The temperature of the assay materials during testing may range from between about zero to about 100 degrees C. In one embodiment, the temperature of the assay materials ranges from between about 10 to about 40 degrees C. Additionally, the temperature of the assay materials may be near room temperature (about 20 degrees C.) and maintained within about ±0.5 degrees C.

Figure 2:
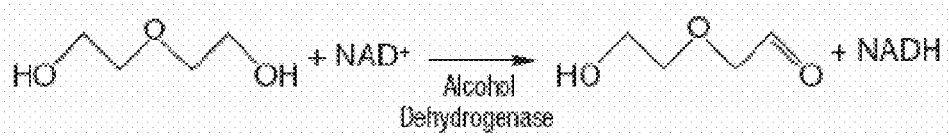
FIG. 2 shows an enzyme reaction pathway used in one embodiment of the invention.

In one set of embodiments, contaminants such as EG and DEG can be detected with an absorbance method 100 (FIG. 1) using a kinetic assay. Absorbance method 100 allows the measurement of concentrations of EG and DEG from below the limits established as safe by the U.S. Food and Drug Administration (FDA) to levels beyond those detected in various historical contamination incidents. In one set of embodiments, absorbance method 100 can convert analytes such as EG and DEG into their respective aldehydes in the presence of yeast alcohol dehydrogenase, as shown in FIG. 1 for EG and FIG. 2 for DEG. In these reactions, the coenzyme NAD+ can be converted to NADH. EG and/or DEG concentrations are determined by monitoring the increase in concentration of NADH, which may be obtained by measuring absorption at about 340 nm using a spectrophotometer.

Figure 3:
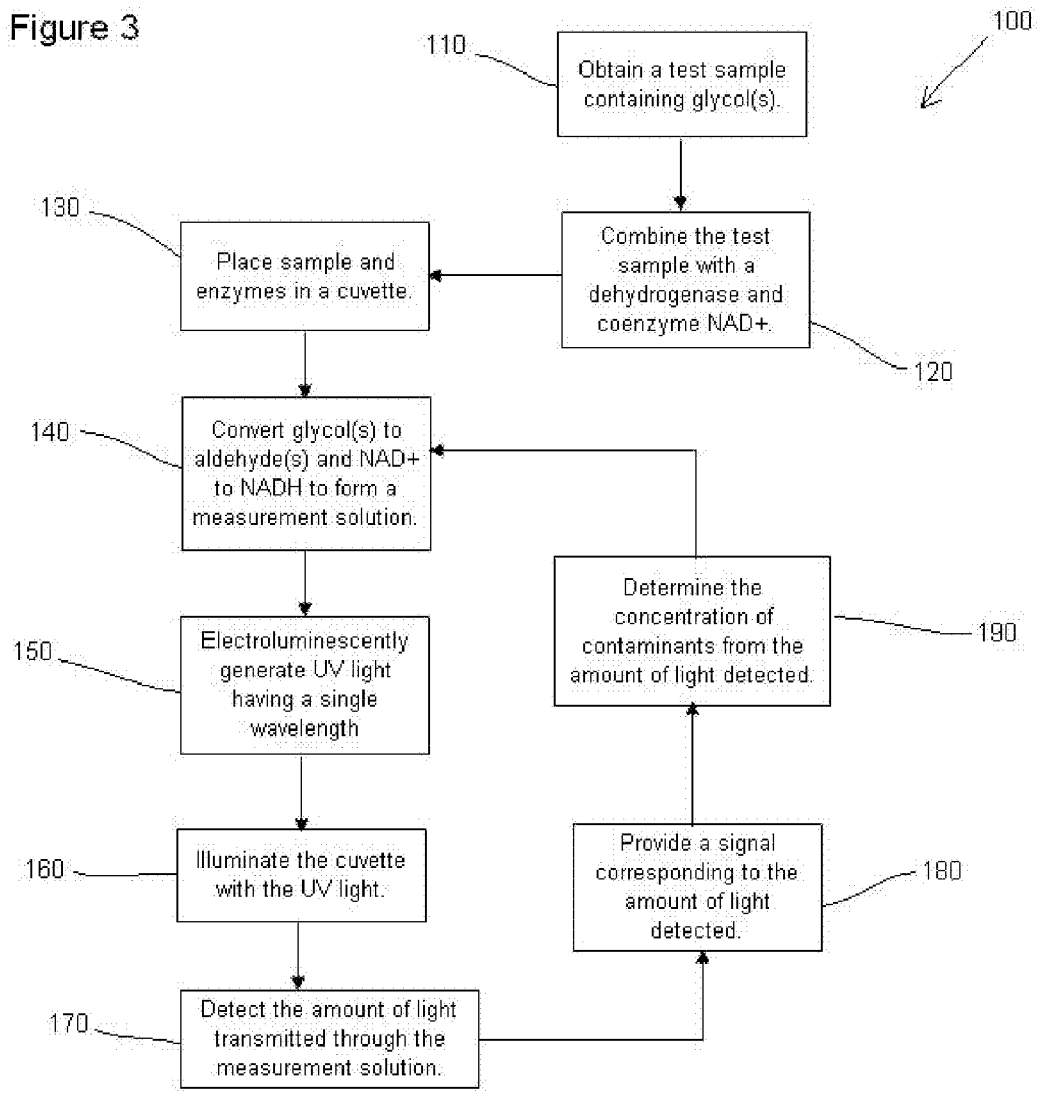
FIG. 3 shows an absorbance method according to one embodiment of the invention.

In one embodiment, shown in FIG. 3, absorbance method 100 begins at step 110 with the collection of a test sample containing one or more glycols. At step 120, the test sample is combined with an enzyme, such as yeast alcohol dehydrogenase, and a coenzyme, such as NAD+. The test sample, enzyme, and coenzyme are placed in a cuvette at step 130. At step 140, the one or more glycols in the sample are converted to one or more aldehydes, and NAD+ is converted to NADH to form a measurement solution. At step 150, a single wavelength light can be electroluminescently generated using a device such as a light emitting diode (LED). At step 160, the cuvette and measurement solution are illuminated with the single wavelength light. At step 170, the amount of light transmitted through the cuvette and measurement solution is detected. At step 180, a signal corresponding to the amount of light detected is provided and at step 190, the concentration of glycol in the sample is determined from the amount of light detected. The absorbance change in this kinetic assay can be proportional to the amount of contamination present.

One or more of steps 110-190 described above and in FIG. 3 may be optional and the order of steps 110-190 may not be important. Additionally, while method 100, as described above, may be used to detect glycol, it may also be used to detect any other contaminants that may include one or more hydroxyl groups.

In a further embodiment, the signal from step 180 may be normalized by the value of the signal at time equals zero. Specifically, the signal may be for example, a voltage, and the voltage at all times may be divided by the voltage at time equals zero. In this way, the background is normalized so that, for example, if the intensity of light generated at step 150 varies from month-to-month, this variation need not affect analytical results. The voltage at time equals zero may be determined by extrapolation if voltages are not available and/or recorded until after that time.

Data from step 180 may be further processed by fitting it with a functional form. In one embodiment, the functional form may be an exponential function, such as $V(t)=1-a*\exp(b*t)$, where V may be the normalized voltage (relative to the voltage at $t=0$), t is time, and a and b are constants to be determined, for example, through a least square curve-fit. Once a functional form as been fit through the time history data, the data may be further analyzed to, for example, extrapolate voltage values to times when measurements were not taken. Additionally, the functional form can be used to, for example, obtain the differences and/or ratios between voltages at different times. The voltage at $t=0$ can be the voltage measured at $t=0$ or can be, for example, the voltage extrapolated to time $t=0$ rather than the actual voltage measured at $t=0$.

The test sample may be heated to drive off certain non-target contaminants or centrifuged prior to being placed in the cuvette. Centrifugation may be used when the sample contains particles such as silicate particles (in toothpaste for example) that can scatter light and interfere with optical measurements.

Embodiments utilizing yeast alcohol dehydrogenase can require relatively large substrate concentrations (e.g., 1.5-1000 mM) to achieve reasonable reaction rates. With yeast alcohol dehydrogenase, the Michaelis-Menten constant, KM, defined as the substrate concentration for half-maximum enzyme activity, is large for both EG and DEG. In order to detect small amounts of substrate quickly, a kinetic assay that measures the initial rate of absorption can be used instead of waiting until the reaction reaches completion and quantifying the overall absorption change. This can provide accurate results in less time than waiting for an endpoint-assay.

Absorbance method 100 may be applied to aqueous solutions having various pH values and ionic strengths. In some embodiments, the pH is maintained between 7 and 9. Repeatable, accurate results have been obtained with pH near 8.0. In one embodiment, absorbance method 100 utilizes buffers such as Tris-HCl. In other embodiments, biocompatible buffers such as phosphate or bicine may be used.

Absorbance method 100 may be used to measure contaminant concentrations in solutions having any temperature between about zero and 100 degrees C. Preferably, the temperature is between about 10 and 40 degrees C. Excellent results have been obtained with the temperature held constant, for instance, within about 1 degree C., such as 26±0.5 degrees C.

For one embodiment of absorbance method 100, an Alcohol-Dehydrogenase-NAD reagent may be prepared from a commercially available kit for ethanol determination (no. 331-CMA; Sigma Chemical Co., St. Louis, Mo. 63178). To an NAD-ADH Multitest Vial (Sigma no. 331-10), 5.3 mL of Tris-HCl buffer, pH 8.8 (Biorad, 0.1M diluted with ddH2 from 1.5M) are added. The resulting composition of the reagent (per liter) is roughly: $1.5 \times 10^5$ U of alcohol dehydrogenase (EC 1.1.1.1), 1.89 mmol of NAD, and 100 mmol of Tris-HCl (pH 8.8). The reagent may be stable for at least 8 hours at room temperature. In a typical measurement, ethylene glycol substrate may be added to the NAD-ADH solution at a ratio 1 to 2 (for example 300 and 600 microliter; or 120 and 240 microliter). The absorbance change may be monitored, for example, for 10 min at 340 nm.

In another set of embodiments, contaminants such as EG and DEG can be detected using a fluorescence method 200 that employs a coupled-enzyme assay to produce changes in fluorescent emission. For example, contaminants such as EG and/or DEG may be used to indirectly convert a fluorogenic substrate (dye) into its fluorescent form, and the concentration of EG and/or DEG can be determined from the amount of light fluorescing from the sample.

Figure 4:
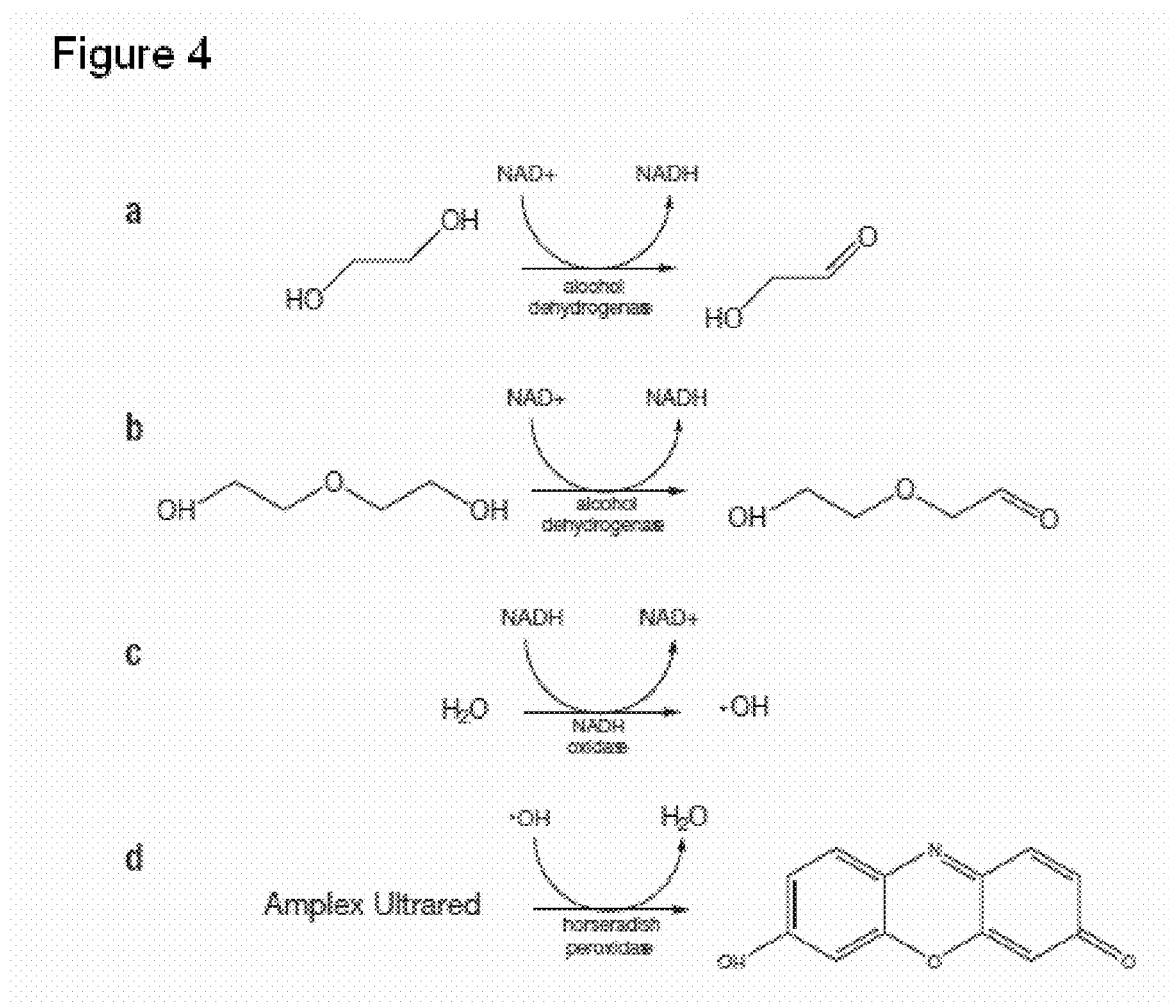
FIG. 4 shows the reactions and enzyme pathways for one embodiment of a fluorescent method.

FIG. 4 illustrates the reactions and enzyme pathways for one embodiment of fluorescence method 200. In reactions a and b, EG and DEG, respectively, are reacted with alcohol dehydrogenase to produce an aldehyde and NADH. By using yeast alcohol dehydrogenase as the particular type of alcohol dehydrogenase, it has been found that interference from the presence of glycerol, propylene glycol, and/or polyethylene glycol may be minimized or eliminated. In reaction c, the NADH may then be converted back to NAD+ with NADH oxidase, which generates one equivalent of hydrogen peroxide for each equivalent of NADH. The hydrogen peroxide may then cleave to create two free radicals. In reaction d, the free radicals, in the presence of horseradish peroxidase (HRP), convert a dye, such as a fluorogenic substrate, from its non-fluorescing form into its fluorescing form. Fluorogenic substrates include materials that can be converted from non-fluorescing to fluorescing forms in the presence of free radicals and a peroxidase. Fluorogenic substrates may be from the resazurin/resorufin family and examples include N-acetyl-3,7-dihydroxyphenoxazine (Amplex Red) available from Invitrogen A36006) and its derivatives and related compounds such as Amplex UltraRed. Peroxidases can include HRP, such as type 1 and type 2.

FIG. 5 illustrates another embodiment of fluorescence method 200 for detecting contaminants such as glycols. At step 210, a sample containing a glycol is collected. At step 212, the glycol is converted to an aldehyde and NAD+ is converted to NADH. At step 214, NADH is oxidized to produce a stoichiometric amount of hydrogen peroxide. At step 216, in the presence of hydrogen peroxide, Amplex UltraRed dye is oxidized with horseradish peroxidase to produce a measurement solution containing resorufin. At step 218, a single wavelength light having a frequency of about 530 nm is electroluminescently generated with, for example, an LED. At step 220, the measurement solution is illuminated with the single wavelength light. At step 222, the amount of light fluoresced from the measurement solution at a different wavelength, about 590 nm, is detected. At step 224, a signal is provided corresponding to the amount of light detected. At step 226, the presence or concentration of glycol is determined. At step 228, a decision can be made about whether or not to continue with the measurements.

One or more of steps 210 through 228 described above and in FIG. 5 may be optional and the order in which the steps occur can be varied. Additionally, while method 200, as described above, may be used to detect glycols), it may also be used to detect any other contaminants having a hydroxyl group. In another set of embodiments, a background subtraction procedure can be performed on the signal from step 224. Specifically, a change in signal between two different time points can be determined by, for example, subtracting the signal at an earlier time from the signal at a later time. For example, if the signal is a voltage, the absolute voltage change between three minutes and eight minutes is the voltage at eight minutes minus the voltage at three minutes. Using this approach, a constant background of fluorescence may be removed, allowing for greater test sensitivity.

Many types of household materials and medicines, such as toothpaste and cough syrup may contain either glycerol or propylene glycol. The tests described herein are able to analyze these samples for EG and DEG without significant interference from glycerol and/or propylene glycol. In other cases, sample preparation may be helpful. While absorbance method 100 and fluorescence method 200 may be used to analyze any type of substrate material, the test sample preparation procedures may depend on the specific type of substrate to be analyzed. For example, when preparing toothpaste samples for fluorescence method 200, the toothpaste samples may be dissolved in buffer and centrifuged. For instance, 3 g of toothpaste sample may be dissolved in 20 ml of Tris-HCl 0.1M pH 7.8 buffer by vortexing the mixture. The sample may then be centrifuged for 10 minutes at 3000 rpm in order to settle out silicate particles that can scatter light and interfere with measurements. The sample may then be further diluted with buffer. Table 1 shows the total amount of buffer that may be added for a given amount of toothpaste and DEG concentration.

TABLE 1

Toothpaste sample preparation.

| wt % DEG | mM DEG | DEG (µl) | toothpaste (µl) | total buffer (ml) |
|---|---|---|---|---|
| 100 | 569 | 135 | 0 | 2.365 |
| 80 | 455 | 108 | 180 | 2.212 |
| 60 | 341 | 81 | 360 | 2.059 |
| 40 | 228 | 54 | 540 | 1.825 |
| 30 | 171 | 40.5 | 630 | 1.830 |
| 20 | 114 | 27 | 720 | 1.753 |
| 10 | 57 | 13.5 | 810 | 1.680 |
| 5 | 28 | 6.7 | 849 | 1.650 |
| 3 | 17 | 4.05 | 873 | 1.623 |
| 1 | 6 | 1.35 | 891 | 1.608 |
| 0 | 0 | 0 | 900 | 1.600 |

When preparing other substrates besides toothpaste, such as cough syrup and allergy syrup, for fluorescence method 200, the sample may be mixed with 0.1M Tris-HCl pH 7.8 buffer. The sample mixture may then be shaken vigorously before usage. Measurement samples may be prepared freshly each day. For viscous samples that are difficult to pipet accurately, such as paracetamol syrup, it may be more practical to weigh out or alternatively predilute the sample with buffer before pipetting it into the mixture. Table 2 shows the total amount of buffer that may be added for a given amount of sample and DEG concentration.

TABLE 2

Sample preparation.

| Wt % DEG | mM DEG | DEG (µl) | sample (µl) | total buffer (ml) |
|---|---|---|---|---|
| 100 | 569 | 135 | 0 | 2.365 |
| 80 | 455 | 108 | 27 | 2.365 |
| 60 | 341 | 81 | 54 | 2.365 |
| 40 | 228 | 54 | 81 | 2.365 |
| 30 | 171 | 40.5 | 94.5 | 2.365 |
| 20 | 114 | 27 | 108 | 2.365 |
| 10 | 57 | 13.5 | 121.5 | 2.365 |
| 5 | 28 | 6.7 | 127.3 | 2.365 |
| 3 | 17 | 4.05 | 130.95 | 2.365 |
| 1 | 6 | 1.35 | 133.65 | 2.365 |
| 0 | 0 | 0 | 135 | 2.365 | in some cases, the analysis may be directed to EG rather than DEG. EG sample preparation may be qualitatively the same as described for DEG in Tables 1 and 2, above. However, since EG may be more reactive than DEG in the presence of yeast alcohol dehydrogenase, smaller concentrations of EG can be employed. Examples of sample concentrations include 0-112 mM EG and corresponding amounts of household product (e.g. toothpaste, cough syrup, paracetamol syrup) to make 0-100 wt % ethylene glycol samples.

In one embodiment of a fluorescence method 200, an Alcohol-Dehydrogenase-NAD-NADH Oxidase reagent may be prepared as follows. First, 15 mL of Tris-HCl buffer pH 7.8 (BM-318 Boston Bioproducts, 0.1M, diluted from 1.0M with ddH20) may be added to an NAD Vial (Sigma Aldrich, 50 mg no. 331-10). Second, a Yeast Alcohol Dehydrogenase (USB/ Affymetrix 10895) stock solution of 1.2 KU/ml may be prepared by diluting. This may be done right before a measurement. Stock solutions may be prepared freshly and need not be frozen down between measurements. Third, a Horseradish Peroxidase Type 1 (Sigma Aldrich P8125-5KU) stock solution of 1000 U/ml may be prepared using Tris-HCl buffer, pH 7.8 (BM-318 Boston Bioproducts, 0.1M, diluted from 1.0M with ddH20). This stock solution may be split up and stored in small vials at −20 degrees Celsius for up to about two months. Before each measurement, one vial of stock solution may be defrosted and diluted to 10 Units/ml using 100 mM Tris HCl buffer (from Boston Bioproducts). Fourth, NADH Oxidase (EMD Chemicals, 481925-5U) stock solution may be prepared by diluting 5 Units of enzyme in 800 microliter of Phosphate Buffer pH 7.4 (Sigma Aldrich P3619-1GA). Aliquots of 100 microliters may be stored in centrifuge tubes at −20 Celsius. Stock solutions may be defrosted between experiments and may be discarded after they have been defrosted. Fifth, Amplex Ultra Red (invitrogen A36006) stock solutions may be prepared freshly before each measurement by diluting a vial of 1 mg Amplex Ultra Red in 400 microliter DMSO (EMD OmniSolv MX1456-6) and vortexing it for several seconds to dissolve the dye.

In a further embodiment, to start the reaction with fluorescence method 200, the measurement sample, a hydrogen peroxidase solution, and the Alcohol-Dehydrogenase-NAD-NADH Oxidase reagent may be combined in a cuvette. 120 microliter of a sample containing, for example, DEG may be added to a plastic cuvette (VWR 97000-586) using a 1 ml pipettor. A new pipette tip may be used for each sample to avoid cross-contamination. Using a 10 microliter VWR pipettor, 3.5 microliter of a 10 U/ml Horseradish Peroxidase Type 1 solution may be injected into each cuvette. A new pipette tip may be used to inject the Horseradish Peroxidase Type 1 solution. To start the reaction, 240 microliter of an Alcohol-Dehydrogenase-NAD-NADH Oxidase reaction mixture may be added to each cuvette. The same tip of the 1 ml pipettor may be used to add the reaction mixture. The Alcohol-Dehydrogenase-NAD-NADH Oxidase reaction mixture, enough for eight cuvettes, may be made of: 1.95 ml NAD, 13 microliter Amplex Ultrared, 6.5 microliter NADH Oxidase, and 40 microliter Alcohol Dehydrogenase. In another embodiment, multiple samples may be run in parallel in separate cuvettes. In addition, 1.95 ml of the Alcohol-Dehydrogenase-NAD-NADH Oxidase reaction mixture may be made freshly before each run and may be mixed thoroughly before starting the reactions.

Coupled enzyme assays often involve different enzymes that function on different substrates and have different pH and temperature optima. With a single enzyme, optimizing activity typically involves selecting only the proper pH, temperature and concentrations of enzyme and substrate, a relatively straightforward task. However, it has been found for the coupled-enzyme reactions described herein the parameter space becomes unpredictable. The concentration of the first enzyme and substrate may be selected so that the resulting product will be in a concentration range that the second enzyme can act upon significantly and without saturation. The product of the second enzyme, a function of the concentrations of both the second enzyme and the product of the first enzyme, should similarly fall in a useful concentration range for the third enzyme, and so forth. Identifying effective concentrations for all of the enzymes and substrates involved is not straightforward as the most effective concentration or conditions for one enzyme may have a deleterious effect on the second enzyme. For example, if the concentration of the product of one enzyme is too low for the next one, no activity will register; conversely, if the concentration of the product of one enzyme is too high, then the activity rate of the next maximum enzyme will limit production of its product. Unless the enzyme activities are comparable, it may not be possible to use a coupled enzyme assay to determine the concentration of a contaminant, such as DEG or EG.

Any test for EG and/or DEG may be subject to a possibility of interference from other glycols, particularly with glycerol and propylene glycol. With several alcohol dehydrogenases from different species, the interference from glycerol and propylene glycol may lead to such high detected activity that the concentrations of DEG and/or EG may not be determined accurately. However, it has been found that one particular alcohol dehydrogenase, yeast alcohol dehydrogenase (USB 10895), may yield a higher activity for higher concentrations of DEG, even in samples with a large fraction of glycerol or propylene glycol.

The pH of the assay mixture may be any value between 4 and 10. In one embodiment, the pH is between 7 and 9. In a further embodiment, the pH is about 7.8.

The concentration of alcohol dehydrogenase may be any appropriate value such as above 5.5 U/mL and in one set of embodiments is near or at 16.5 U/mL. The concentration of NAD may be any value above 0.7 mg/mL and in one set of embodiments is near or at 2.22 mg/mL. The concentration of NADH oxidase may be any value above 4.5 mU/mL and may be, for example, at or near 14.1 mU/mL. The concentration of HRP may be any value above 35 mU/mL but preferably is at or near 97.2 mg/mL. The concentration of Amplex Ultrared may be any value above 4 mg/L but in a preferred embodiment is at or near 11.3 mg/L.

Alcohol dehydrogenase (ADH), and indeed many or all dehydrogenases, are capable of converting OH groups to aldehydes. It has been found that alcohol dehydrogenase acts very efficiently on methanol (with one carbon) and ethanol (with two carbons), for which it originally evolved in biological organisms. It acts on other alcohols, as well, and on glycols, compounds with multiple OH groups. Its activity on ethylene glycol (two carbons) may be expected, and the lower activity rate acting on DEG may also be expected, which with four carbons has a higher molecular weight. We may therefore expect that alcohol dehydrogenase would have a comparable, if not faster, rate of activity on three-carbon propylene glycol and glycerol. Using an alcohol dehydrogenase to detect DEG in the presence of glycerol and propylene glycol may therefore not be expected to work due to interference from these compounds; by contrast, given the high reactivity rate of EG with ADH, we may expect higher rates of activity for propylene glycol and glycerol, relative to DEG. However, as the methods described herein reveal, with a certain type of ADH, the concentration of DEG can be detected and quantified, even in the presence of propylene glycol and glycerol.

For a given enzyme, there exists an optimal set of conditions for activity, in particular temperature and pH. The assays described above may be run at room temperature (approximately 25 degrees C.) even though this may not be the optimum temperature for these reactions. Slight variations in room temperature (i.e. in the range of 20-25 deg C.) may not affect the results significantly. When running a single-enzyme reaction, such as the single alcohol dehydrogenase reaction, a pH is selected that maximizes activity. The optimal pH range for each enzyme used in the above assays may be found in the literature. However, when these optimal ranges are not the same for each enzyme used in a coupled assay, the coupled reaction may not succeed because the enzymes may be incompatible. For example, enzymes in the wrong pH conditions may be unstable, and can disintegrate. For instance, placing an acid-optimized enzyme in a highly alkaline environment, in many cases, will denature that enzyme, causing it to lose its proper structure and render it incapable of functioning at all. In particular, alcohol dehydrogenase has maximum activity at pH 9.0, well in the alkaline regime; at pH 8.0, its activity is 10% of the maximum. By contrast, NADH oxidase has maximum activity at an acidic pH of 6.5. Coupling the product of an alcohol dehydrogenase reaction, ideally performed in an alkaline environment, to a reaction involving NADH oxidase, which should be run in an acidic environment, may not be expected to work. Horseradish peroxidase is even more acidophilic, having an optimal pH range of 5 to 7. There are different ways to solve this problem. The product from the first alcohol dehydrogenase reaction could be isolated, purified, and then reintroduced into a reaction under conditions optimal for NADH oxidase; however, this isolation and purification is impractical for a portable device, such as device 400, both in terms of cost and complication. Alternatively, for a "one-pot" reaction, a single set of conditions under which the enzymes operate well enough may not be expected, let alone guaranteed, to exist. For the methods disclosed herein the reactions are run at a pH that is outside the optimum range for all of the enzymes involved.

Figure 6A:
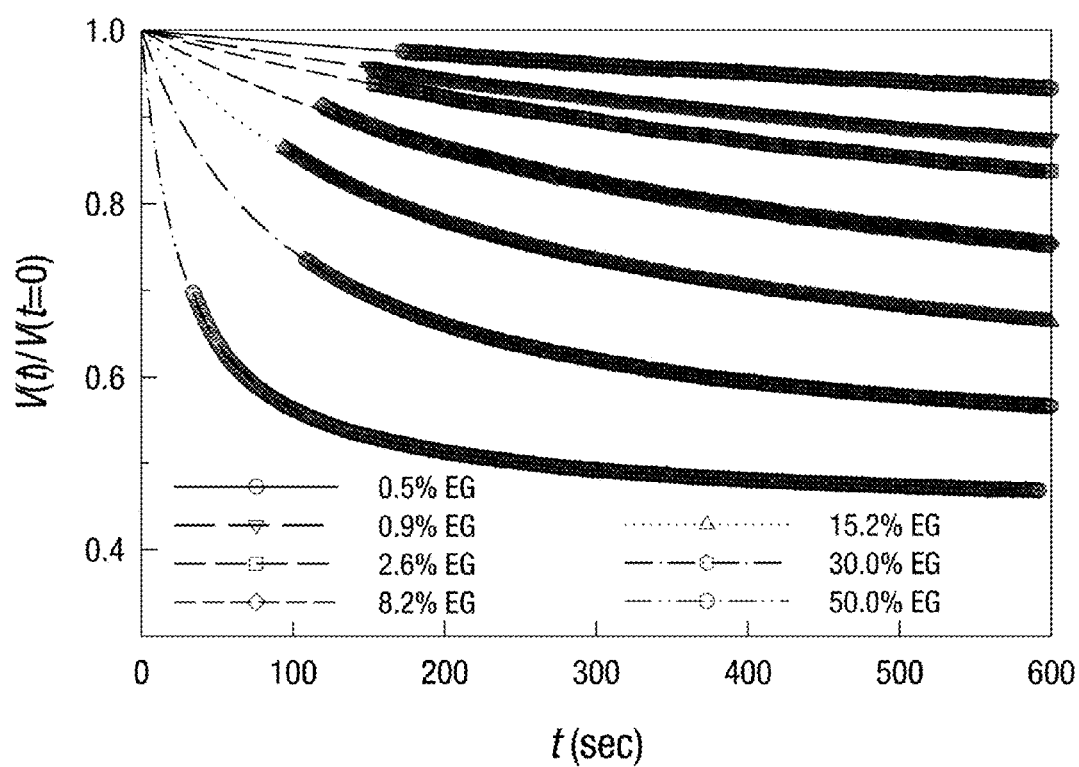
FIG. 6a is a plot of voltage versus time according to one embodiment of the invention.

FIG. 6a provides a photocopy of a plot of voltage output from a light detector versus time, for various concentrations of EG, as obtained with absorbance method 100. As shown, with absorbance method 100, output voltage may decrease in an exponential decay manner, with more rapid decay occurring with higher glycol concentrations. The voltage at all times may be divided by the voltage at time equals zero. In this way, the background is normalized so that, for example, if the intensity of light generated at step 150 varies from month-to-month, this variation may not affect analytical results. The voltage at time equals zero may be determined by extrapolation if voltages are not available and/or recorded until after that time.

Figure 6B:
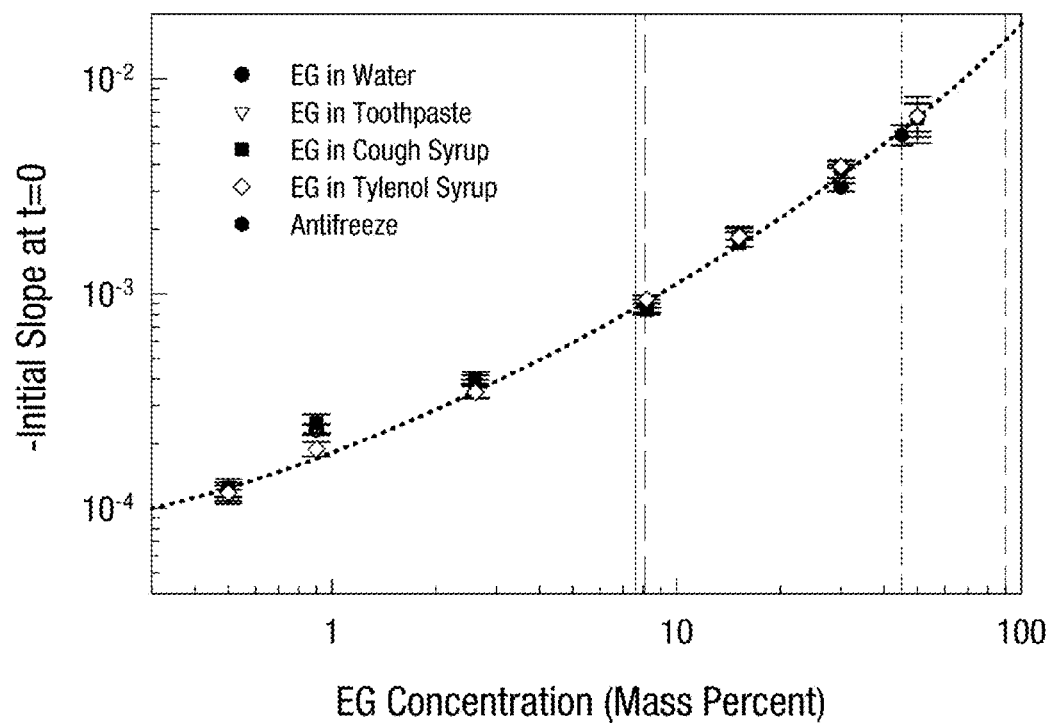
FIG. 6b is a plot of normalized enzyme activity versus ethylene glycol concentration according to one embodiment of the invention.

The rate of voltage change may provide an indication of glycol concentration. For example, FIG. 6b provides a photocopy of a plot of the rate of voltage change, $-dV/dt$, at time equals zero for various substrates and EG concentrations, where V is the raw voltage normalized by its value at time equals zero. As shown, the initial rate of voltage change may increase with EG concentration. Also, measurement results may be insensitive to the type of substrate being tested, since the results in FIG. 6b for water, toothpaste, cough syrup, paracetamol syrup, and antifreeze are nearly identical. For reference, FIG. 6b also includes vertical lines indicating the EG concentrations associated with mass poisonings in Panama and Nigeria and the EG concentration of antifreeze (about 45 percent). It is also notable that most of these samples contained propylene glycol at levels up to 30% and the testing procedure did not provide false positive results under these circumstances.

Figure 7A:
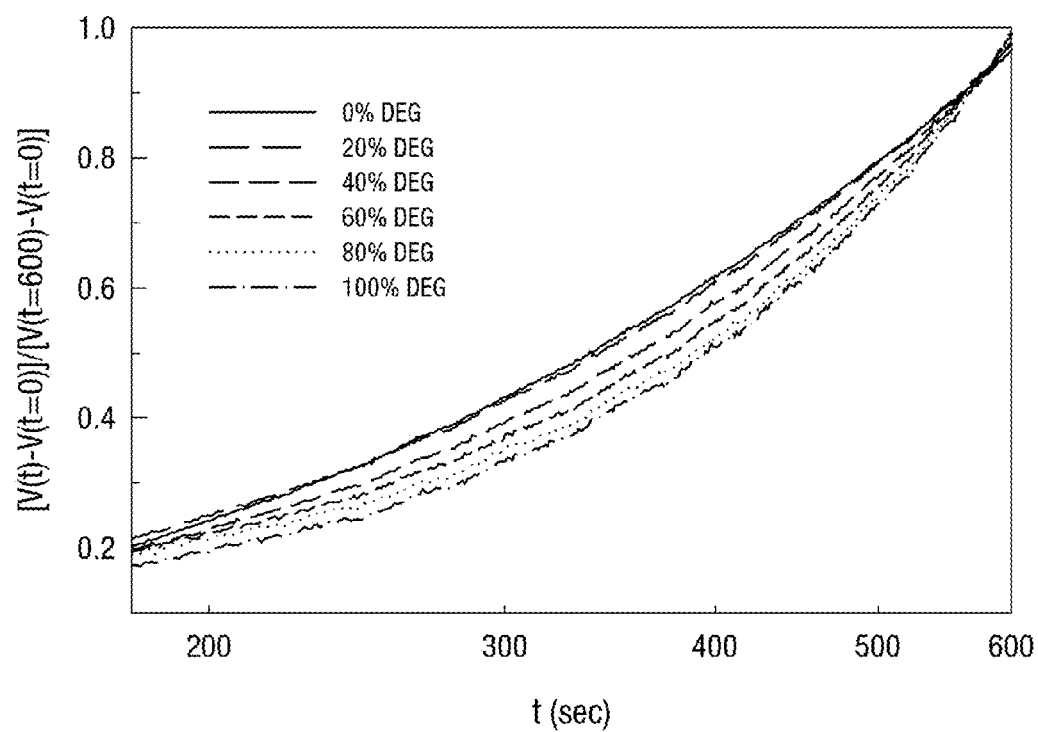
FIG. 7a is a plot of voltage versus time according to one embodiment of the invention.

FIG. 7a provides a photocopy of a plot of voltage output from a light detector versus time, for various concentrations of DEG, as obtained with fluorescence method 200. As shown, with fluorescence method 200, output voltage may increase over time in an exponential growth manner. In addition, exponential growth may occur even when the DEG concentration is zero percent, possibly due to the presence of a small amount of NADH in thermal equilibrium, which in turn may drive the production of the fluorogenic substrate into its fluorescent form.

In one embodiment, the output voltage from a light detector is measured as a function of time. For example, in a typical measurement, output voltage may be recorded about once per second. In addition, voltage may be recorded beginning about three minutes after the reaction is started and ending about 10 minutes after the reaction is started. The voltage measured by the detector for the first ten minutes after mixing may conform to a functional form $$V_{fl} = \beta \exp(t/\tau_{fl}) + V_0$$

where $V_0$ is the baseline, constant voltage for the detector, which can be measured, for example, with a water-filled cuvette. Different concentrations of EG and/or DEG yield different values of the enzyme activity, manifest as the characteristic time constant $\tau_{fl}$. However, due to variations in the activity of the different enzymes, and the chemical amplification of the signal, variations of up to ±20% of the absolute enzyme activity may occur for different measurements of the same sample under ostensibly identical conditions.

To minimize such measurement errors, for both absorbance method 100 and fluorescence method 200, measurements may be performed simultaneously on multiple devices and results may be normalized. For example, a test sample may be measured in one device and a sample of 100 percent DEG (standard) may be simultaneously measured in another device. Enzyme activity values may be determined from these measurements, and the time constant resulting from the enzyme activity value for the test sample, $\tau_{fl}$, can be divided by the time constant resulting from the enzyme activity for the 100 percent DEG sample, $\tau_{fl}^{100\%}$, to obtain a normalized enzyme activity $$\tau' = \tau_{fl}/\tau_{fl}^{100\%}.$$

Figure 7B:
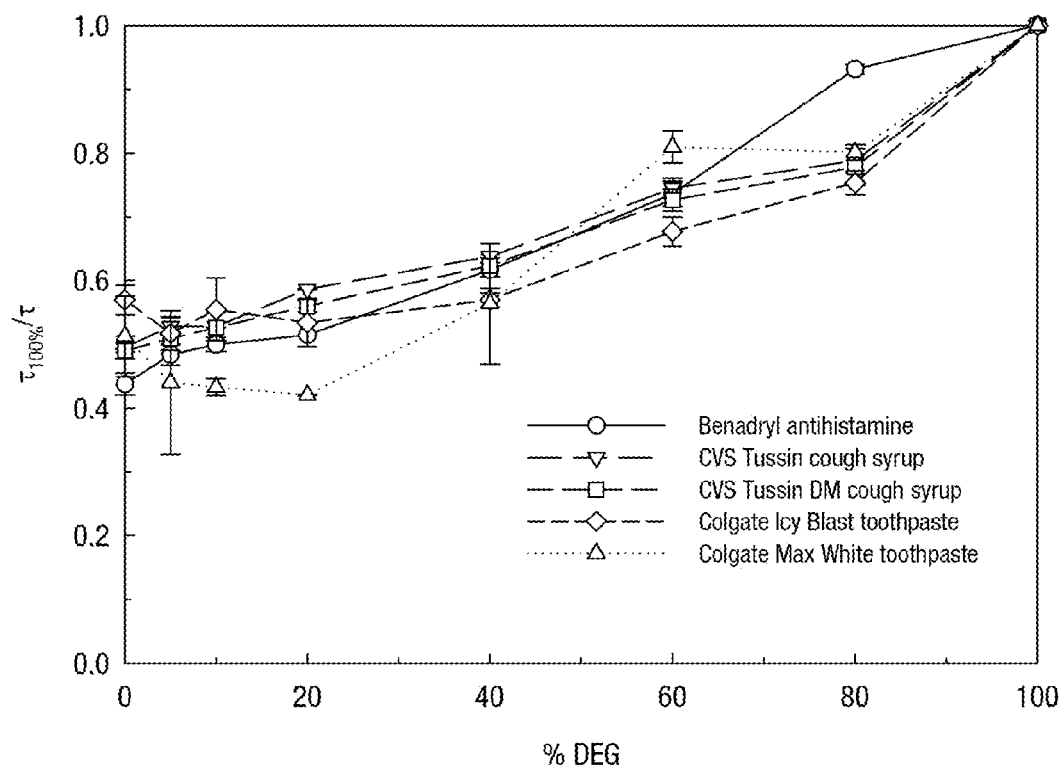
FIG. 7b is a plot of normalized enzyme activity versus diethylene glycol concentration according to one embodiment of the invention.

With this multi-detector strategy and normalization, the normalized enzyme activity is monotonically correlated with the concentration of DEG, even in the presence of glycerol and propylene glycol, for a range of household products and medicines, as shown in FIG. 7b. FIG. 7b is a plot of normalized enzyme activity versus DEG concentration, as obtained with fluorescence method 200, for various household products and medicines.

For both absorbance method 100 and fluorescence method 200, described above, it may be desirable to heat certain test samples prior to measuring them. For example, when alcohol dehydrogenase is used as an enzyme, ethanol can be removed from the sample liquid prior to mixing with the buffer solution. In one embodiment, ethanol may be removed by heating the sample above the boiling point of ethanol (78.4° C.). For example, the sample may be heated in a microfluidic channel using a vapor permeable polymer membrane such as polydimethylsiloxane or Nafion. In addition, the gums and particles present in materials such as toothpaste can interfere with measurements. In one embodiment, these gums and particles are degraded by placing the test sample in boiling water for about 10 minutes.

In one aspect, a device is provided that can quantify light absorbance and/or fluorescence using single-wavelength illumination and photodiode detection. The device may include a plastic housing that precisely holds the illumination and detection components in place, ensuring that the relative positions of these components and the sample cuvette are the same over time, in order to achieve reproducible measurements. The device may be manufactured and assembled at far less cost than traditional laboratory fluorometers and spectrophotometers. It may be battery powered and therefore completely portable. It may also include two complimentary halves that may be molded identically with each half constructed and arranged to hold a standard 1 cm cuvette, and where the two halves may be snapped together to form a single double-sided instrument that can simultaneously measure two samples.

Figure 8:
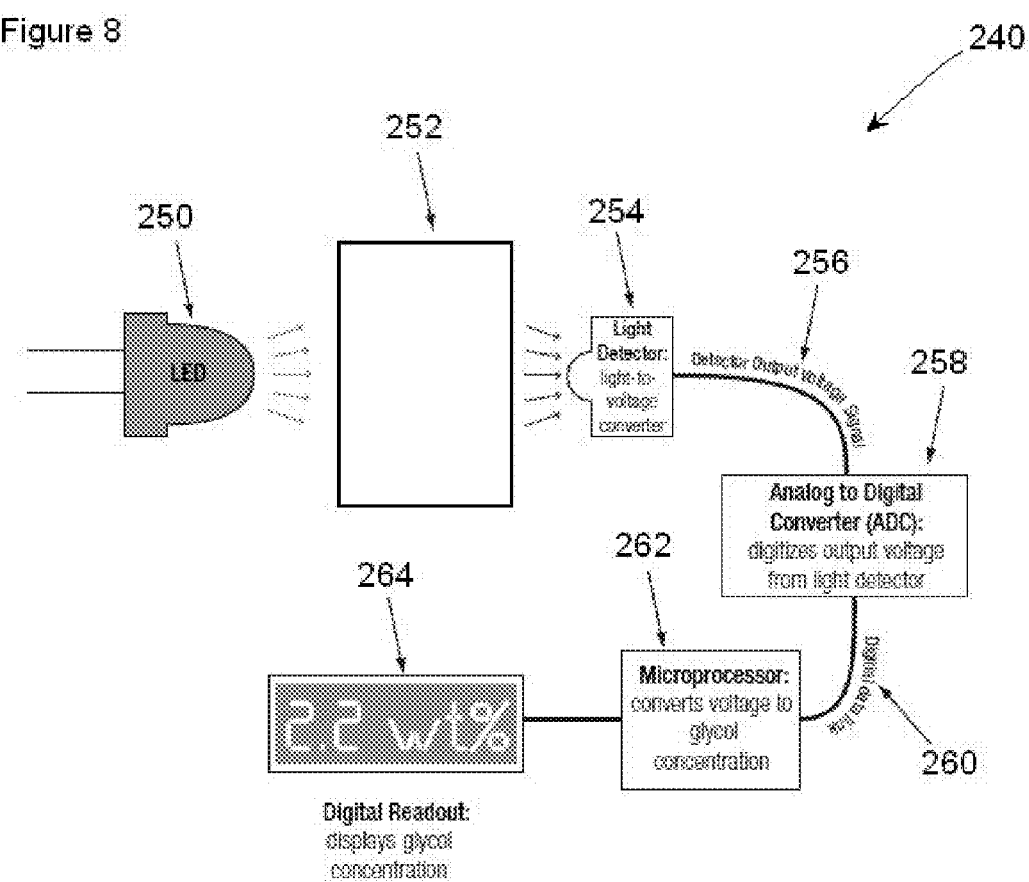
FIG. 8 is a schematic of a detector according to one embodiment of the invention.

FIG. 8 schematically illustrates one embodiment of a low-cost, single wavelength meter 240 that may be used with absorbance method 100 and/or fluorescence method 200 described above. Meter 240 consists of a light source 250, a cuvette 252 containing a measurement sample, and a light detector 254. Light source 250 illuminates cuvette 252, and light detector 254 detects the amount of light exiting from a portion of cuvette 252.

The light generated with light source 250 may be a single wavelength light. Such light may be generated using an electroluminescent device such as an LED or a laser. Light source 250 may be chosen so that the generated range of wavelengths is located near the peak absorption of a product of enzyme activity, such as NADH. NADH has peak absorption at about 362 nm. In that case, the light may be UV with an emission peak at about 365 nm. Light source 250 may also be chosen so that the generated range of wavelengths is located near the peak excitation frequency of a fluorescent material. For example, when Amplex Ultrared fluorescent dye is used, the light may be green and have an emission peak at about 527 nm.

Light detector 254 generates a time-dependent voltage 256 proportional to the amount of light received. Voltage 256 may be recorded with a voltmeter or similar device and converted to a digital signal using an analog-to-digital converter 258. Analog-to-digital converter 258 may be connected using a digital data link 260 to a microprocessor 262. Microprocessor 262 may be programmed to convert the digital signal to the concentration of contaminants, such as EG and/or DEG. Finally, a digital readout 264 may be used to display the results, such as measured concentration, from microprocessor 262.

When used with absorbance method 100, described above, the voltage from light detector 254 may decay exponentially over time. In a kinetic assay, the initial rate of this decay is directly proportional to the amount of contaminant, such as EG and/or DEG, present in the sample. As a result, meter 240 may be capable of detecting contaminants in a short amount of time (e.g., less than 30 minutes, less than 20 minutes or less than 10 minutes).

Figure 9:
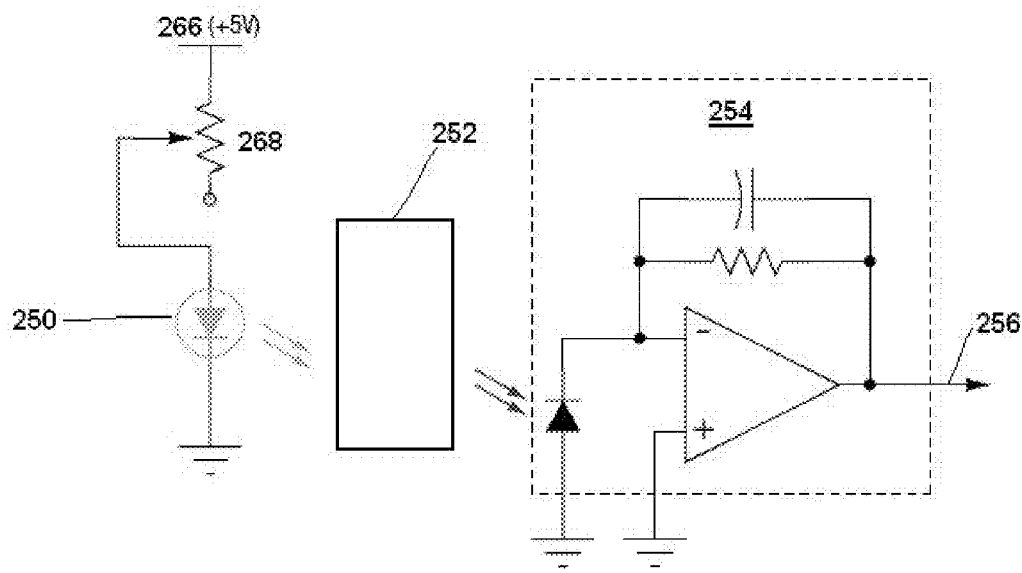
FIG. 9 is a circuit diagram of a detector according to one embodiment of the invention.

A circuit diagram for an embodiment of meter 240 is shown in FIG. 9. Meter 240 may be driven by a 5V power supply 266, which may be provided either with AC power stepped down through a power regulator (not shown), or DC power with, for example, several batteries. Light source 250 may be connected to a variable resistor 268 so that the amount of light generated can be adjusted, if desired. The light passes through cuvette 252 and strikes light detector 254 to produce voltage 256.

Meter 240 may be less expensive than traditional analytical optical instruments, such as a spectrophotometer. One reason for the high cost of traditional instruments is that they have the ability to generate precise wavelengths of light over a very large range. While this flexibility is needed to analyze the wide range of samples and reactions that might be encountered, it is not needed to analyze the reactions that occur with absorbance method 100 and fluorescence method 200, described above, where the optical properties of the materials to be detected are already known. In the latter situation, single wavelength light sources may be used, thereby avoiding the far more expensive and complicated lamp and diffraction-grating pairing found in spectrophotometers.

The NADH absorption method, described above, is particularly amenable to a single wavelength approach. NADH has a broad absorption peak, centered at about 340 nm, so that light transmission measured at 340 nm should provide the most sensitive results. It has been found however that wavelengths in the 350-360 nm range also can yield useful results. Light over this range of wavelengths can be produced by frequency-tripled Nd:YAG and Nd:YVO4 lasers (which cut the original 1064 nm wavelength into 3, yielding a 355 nm beam) are relatively low-cost and can generate large amounts of power. In addition, LEDs that generate around a milliwatt of power in the 360 nm range are available at relatively low cost.

In addition to an inexpensive light source, meter 240 may include other inexpensive components. For example, light detector 254 may be a TSL257-LF photodiode from TAOS. In addition, analog-to-digital converter 258, microprocessor 262, and digital readout 264 can be combined into a single low-cost, low power microprocessor, such as the MSP430 series from Texas Instruments. By using such items, meter 240 can be produced at far less cost than a traditional spectrophotometer. Additionally, meter 240 may be built in a handhold form and readily implemented in tough field environments.

Figure 10:
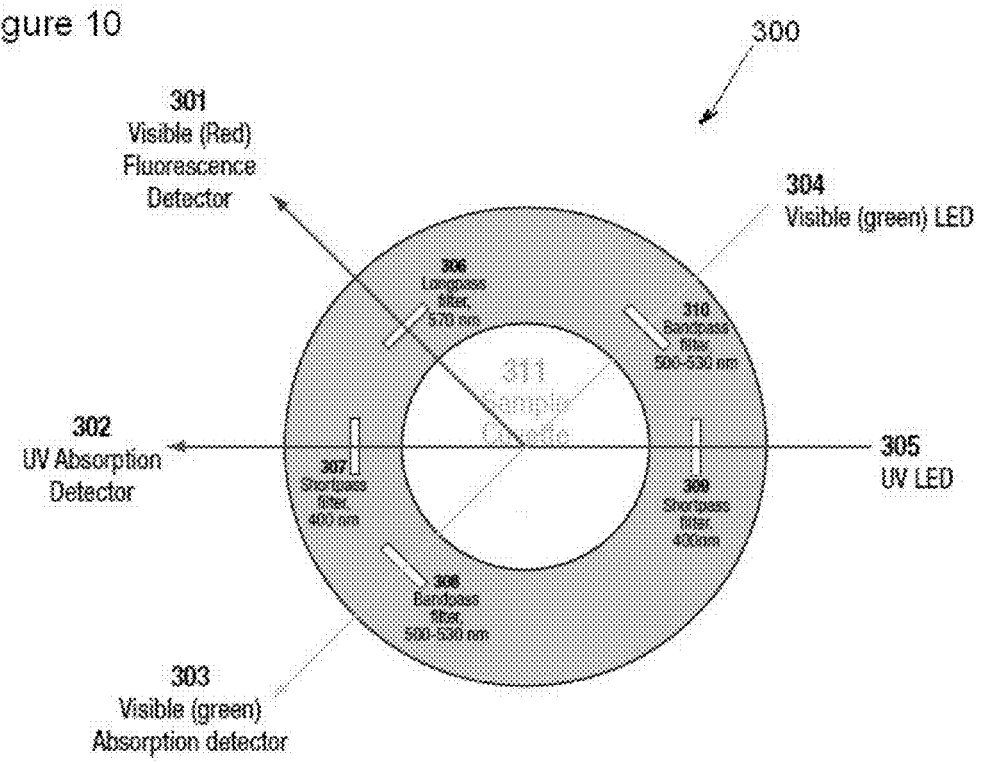
FIG. 10 shows an arrangement of light sources and light detectors according to one embodiment of the invention.

FIG. 10 schematically illustrates an embodiment of a device 300 capable of measuring light absorbance and light fluorescence at the same time. Device 300 may be used to perform measurements for absorbance method 100 and/or fluorescence method 200, described above. Device 300 combines a fluorescence detector 301, a UV light detector 302, a green light detector 303, a green LED 304, a UV LED 305, and a cuvette 311. Cuvette 311 may contain a measurement sample. Green LED 304 and UV LED 305 shine light into cuvette 311. Fluorescence detector 301, UV light detector 302, and green light detector detect light received from cuvette 311.

Green LED 304 may be used for both absorbance and fluorescence measurements. Green LED 304 shines a single-wavelength green light into cuvette 311. For absorption measurements, green light detector 303, located on the opposite side of cuvette 311 from green LED 304, detects the amount of green light from green LED 304 that passes through measurement sample and cuvette 311. For fluorescence measurements, a fluorescence detector 301 detects the amount of red light fluoresced from the measurement sample within cuvette 311.

Green LED 304 may be chosen so that the emission peak of the green light is within the excitation peak of the fluorescent dye used for fluorescent method 200. For example, in one embodiment, green LED 304 may have an emission peak at about 527 nm, which falls within the excitation peak of Amplex Ultrared. In addition, the emission peak of green LED 304 may be near an absorption peak of the fluorescent dye used for fluorescent method 200. For example. Amplex Ultrared dye has strong absorption in the green. Therefore, when green LED 304 has an emission peak at about 527 nm, green LED 304, used in conjunction with Amplex Ultrared dye, may be suitable for both fluorescence and absorption measurements.

Because fluorescence may be isotropic, the intensity of fluoresced light from cuvette 311 could be nearly independent of the angle at which fluorescence detector 301 is placed relative to the light beam from green LED 304 used for excitation. Fluorescence detector 301 may therefore be placed at any angle with respect to the light beam. For example, as shown in FIG. 10, fluorescence detector 301 may be placed at nearly ninety degrees from the incoming beam path generated by green LED 304, thereby increasing the signal-to-noise ratio of the detected fluorescence emission.

For the purposes of absorption measurements, device 300 may also include a UV LED 305. UV LED 305 can generate and send a single-wavelength UV light into cuvette 311. A UV light detector 302, located on the opposite side of cuvette 311 from UV LED 305, detects the amount of UV light from UV LED 305 that passes through measurement sample and cuvette 311.

UV LED 305 may be chosen so that it has an emission peak near the absorption peak of a reactant and/or a product of a chemical reaction. For example, UV LED 305 may have an emission peak near about 365 nm because NADH, a product of the enzyme reactions in FIG. 4, absorbs strongly near that wavelength.

In another embodiment, to improve the accuracy of absorption and fluorescence measurements, device 300 may include longpass filter 306, shortpass filter 307, and bandpass filter 308. Filters 306, 307, 308 may improve the signal-to-noise ratio by preventing unwanted light from reaching fluorescence detector 301, UV light detector 302, and green light detector 303. For example, bandpass filter 308 may be placed between green light detector 303 and cuvette 311 so that only green light can impact green light detector 303. In addition, shortpass filter 307 may be placed between UV light detector and cuvette 311 so that only UV light can impact UV light detector 302. Finally, longpass filter 306 may be placed between fluorescence detector 301 and cuvette 311 so that only fluoresced light can reach fluorescence detector 301.

To further improve the signal-to-noise ratio, device 300 may also include a shortpass filter 309 located between UV LED 305 and cuvette 311, and a bandpass filter 310 located between green LED 304 and cuvette 311. Bandpass filter 310 may allow only green light to reach cuvette from the vicinity of green LED 304. Shortpass filter 309 may allow only UV light to reach cuvette 311 from the vicinity of UV LED 305.

To ensure accurate and reproducible measurements, the relative positions of the illumination sources, sample cuvette and detectors should be carefully maintained over time. In a laboratory fluorometer, these components are mounted in a precisely-manufactured housing that would be too delicate and expensive for field use. Therefore, to reduce costs and improve durability, the holder for samples and optics may be fabricated from a precision injection molded plastic to provide for precise and repeatable alignment of cuvettes in a portable device.

Figure 11:
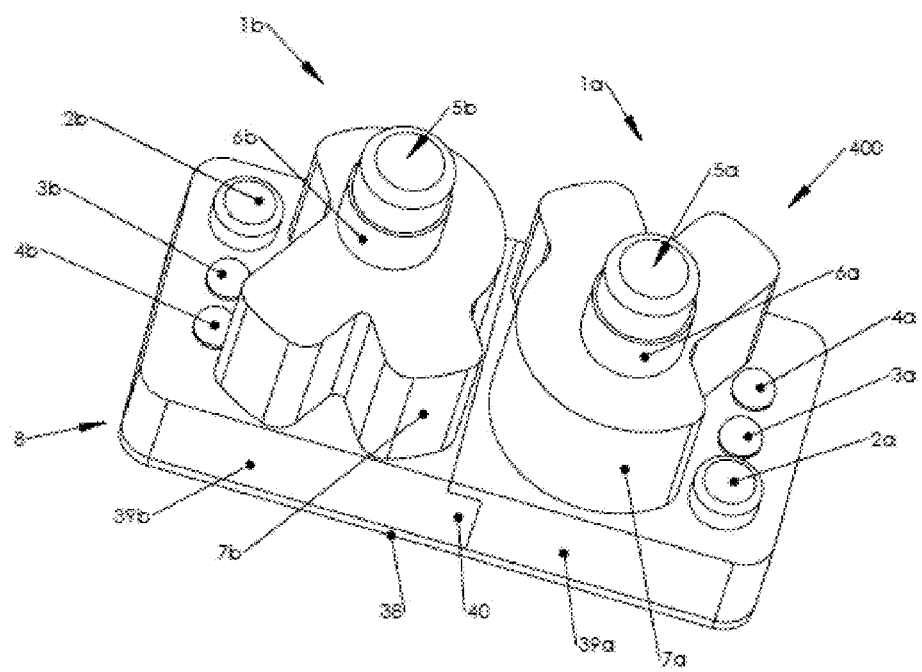
FIG. 11 is an isometric view of a measurement device according to one embodiment of the invention.

FIG. 11 shows one embodiment of a device 400 that includes identical molded halves 1a and 1b. Molded halves 1a and 1b each include sensor holding structures 7a, 7b, buttons 2a, 2b, and indicators 3a, 3b, 4a, 4b. Sensor holding structures 7a, 7b include sample holder receivers 6a, 6b. Molded halves 1a and 1b may be made of any solid material or combination of solid materials. For example, molded halves 1a and 1b may be made of one or more types of plastic such as polystyrene, polypropylene, ABS, polyurethane, polyethylene, polyamide (Nylon), or polyacetal (DELRIN®).

Device 400 may be used to simultaneously measure two separate samples. For example, molded half 1a may be used to measure a reference sample, and molded half 1b may be used to measure a test sample. These two samples may be measured concurrently or in sequence. A cuvette having a cap 5a and containing the reference sample may be inserted into sample holder receiver 6a, and a cuvette having a cap 5b and containing the test sample may be inserted into sample holder receiver 6b. Measurements may be initiated by pressing buttons 2a and/or 2b.

Indicators 3a, 3b, 4a, and 4b may indicate the presence or absence of contaminants in the cuvettes. For example, indicators 3a and 3b may be red and may illuminate if a contaminant is detected in one or both of the cuvettes. Similarly, indicators 4a and 4b may be green and may illuminate if no contaminants are detected in one or both of the cuvettes. Indicators 3a, 3b, 4a, 4b may be illuminated using, for example, LEDs. Buttons 2a and 2b and indicators 3a, 3b, 4a, 4b may be mounted to a circuit board 20 in a base 8 of device 400.

Figure 12A:
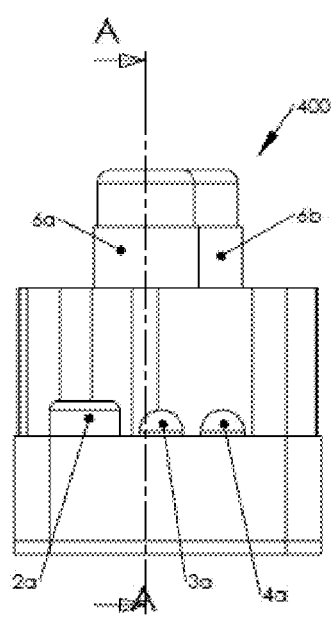
FIG. 12a is a side view of a measurement device according to one embodiment of the invention.
Figure 12B:
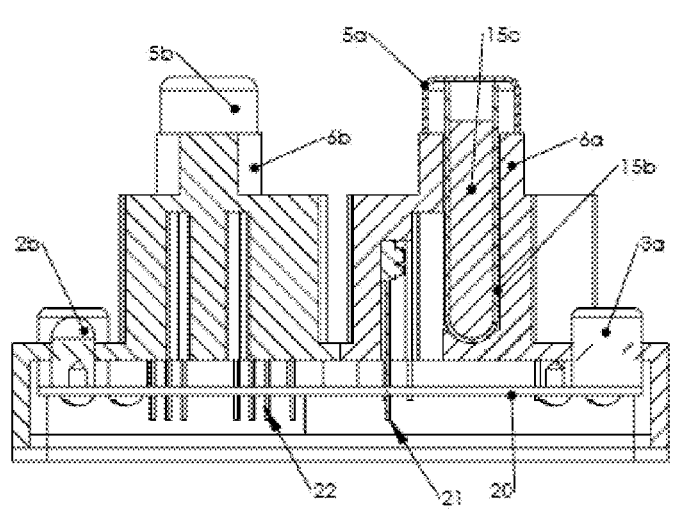
FIG. 12b is a section view of a measurement device according to one embodiment of the invention.

FIG. 12a is a side view of device 400 and FIG. 12b is a section view in which circuit board 20 can be seen. Each molded half 1a, 1b of device 400 includes a green LED 29b, a UV LED 29A, a green light detector 31b, a UV light detector 31c, and a fluorescence detector 31a. These LEDs 29b, 29a and detectors 31b, 31c, 31a may be connected to circuit board 20 with leads 21, 22. Circuit board 20 may also contain (not shown) the basic circuits needed to control LEDs 29b, 29a and process signals from detectors 31b, 31c, 31a. A reference sample 15c in a cuvette 15b may be prepared and inserted into sample holder receiver 6a. Similarly, a test sample may be inserted into sample holder receiver 6b.

Figure 13:
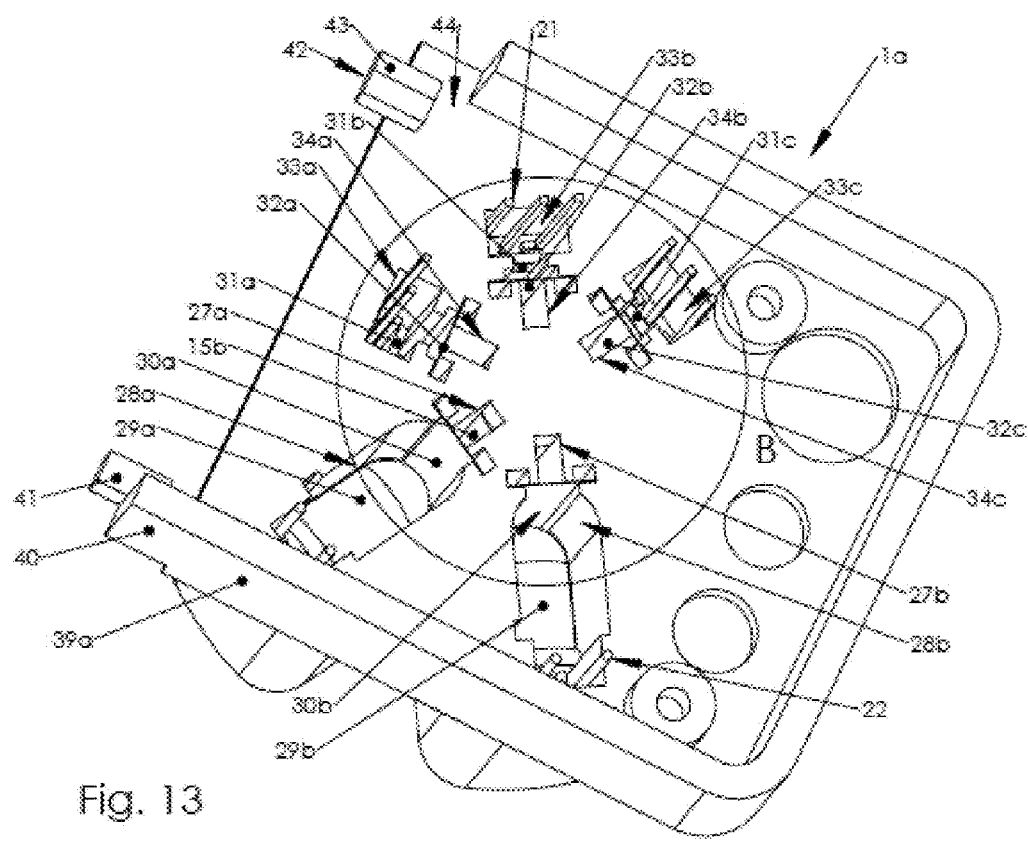
FIG. 13 is a bottom isometric view of a measurement device according to one embodiment of the invention.
Figure 14:
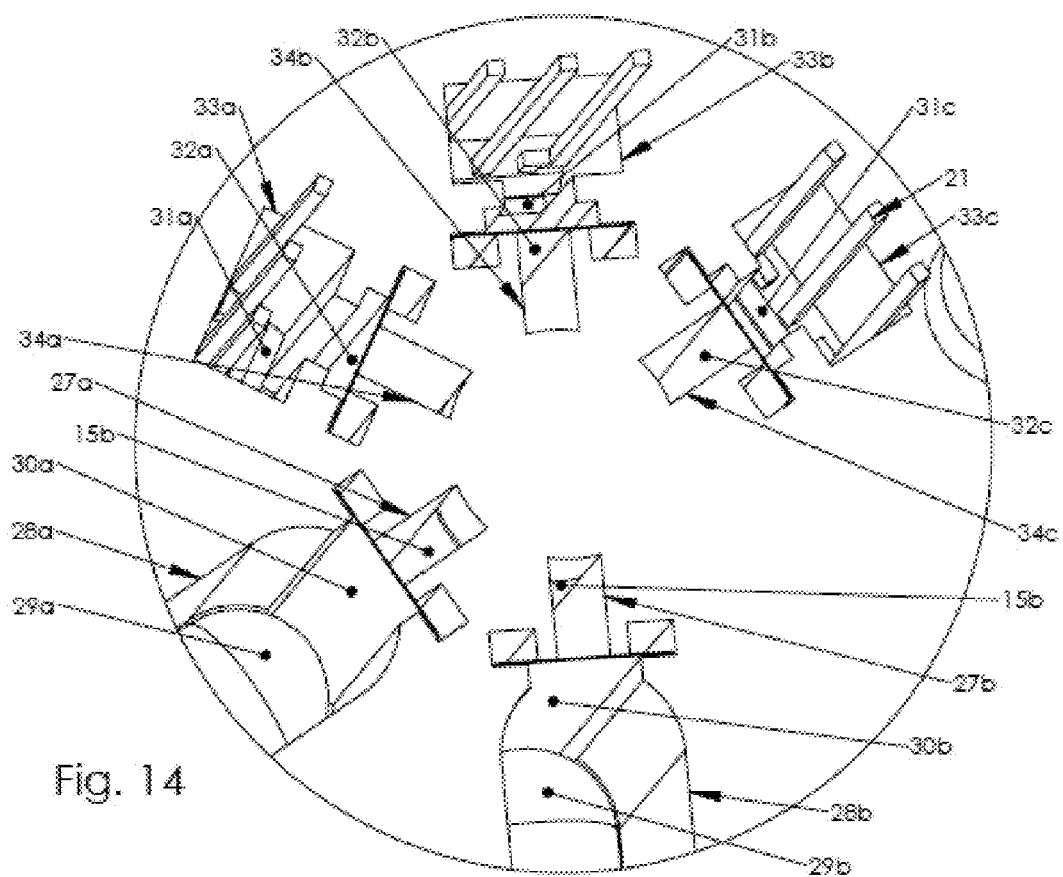
FIG. 14 is a bottom isometric view of a measurement device according to one embodiment of the invention.

FIGS. 13 and 14 show a bottom isometric view of molded half 1a. Molded half 1a includes LED pockets 28a, 28b and detector pockets 33a, 33b, 33c. LED pockets 28a, 28b contain green LED 29b and UV LED 29a. Green LED 29b, may be, for example, of the type having CREE's model number LC503FPG1-15P-A3, UV LED 29a may be, for example, of the type having LED Supply's model number L5-0-U5TH15-1. Detector pockets 33a, 33b, 33c contain green light detector 31b, UV light detector 31c, and fluorescence detector 31a. One or more of green light detector 31b, UV light detector 31c, and fluorescence detector 31a may be TAOS's TSL257 high-sensitivity light-to-voltage converter. These LEDs and detectors may be identical to those shown in devices 240 and 300.

In another embodiment, device 400 also includes filters 32a, 32c, 32b, 30a, 30b and focusing slits 34a, 34c, 34b, 27a, 27b. To reach green light detector 31b, light from green LED 29b passes through filter 30b, focusing slit 27b, cuvette 15b, focusing slit 34b, and filter 32b. To reach UV light detector 31c, light from UV LED 29a passes through filter 30a, focusing slit 27a, cuvette 15b, focusing slit 34c, and filter 32c. To reach fluorescence detector 31a, light fluoresced from the measurement sample passes out of cuvette 15b, through focusing slit 34a, and filter 32a. Focusing slits 34a, 34c, 34b, 27a, 27b may help to spatially constrain the light, and may be shaped, for example, as slits and/or pinholes.

Signals from detectors 31b, 31c, 31a may be processed on circuit board 20, as described previously, and if one or more contaminants are present indicators 3a, 3b may light up. If no contaminants are present, indicators 4a, 4b may light up.

Filters 32a, 32c, 32b, 30a, 30b may be made of clear plastic filter material. The material may be, for example, of the inexpensive type often used for theatre lighting. The filter material can be die cut to the desired size to fit into pockets 28a, 28b. For a sense of scale, green LED 29b and UV LED 29a may each be about 5 mm diameter, and filters 32a, 32c, 32b, 30a, 30b may be about 0.5 mm thick, 5 mm wide, and 20 mm long.

To improve measurement accuracy, LEDs 29b, 29a and detectors 31b, 31c, 31a may be secured in place with adhesive and/or a piece of compressible material such as foam rubber stuffed in LED pockets 28a, 28b and/or detector pockets 33a, 33b, 33c. The foam rubber may also help isolate the LEDs 29b, 29a and detectors 31b, 31c, 31a from stray light. Circuit board 20 may be pre-drilled with either press-fit connectors for leads 21, 22 so the board can be removed, or leads 21, 22 can poke through plated vias to be soldered into place. If circuit board 20 has to be removed, leads 21, 22 may be desoldered.

The modular design of device 400 allows two identical molded halves 1a and 1b to be combined to make the instrument body. Molded halves 1a and 1b have skirts 39a and 39b that form a pocket for the circuit board when the two halves are assembled. To provide alignment, as shown in FIG. 13, tabs 40 and 41 can mate with corresponding tab 42 and surface 44 by placing molded halves 1a, 1b face-to-face but rotated with respect to each other, and then twisting molded halves 1a, 1b until tabs 40, 41, 42 seat. Round 43 helps to allow the twist-and-seat motion to occur. An adhesive can be applied before assembly, or the presence of a screwed-down circuit board 20 and a snapped-in place bottom cap 36 can hold the instrument together.

Standalone fluorometers typically involve a single sample cuvette. It is not possible to run multiple samples at the same time (as is possible on a plate reader, a large, sophisticated and expensive piece of equipment that has never been made portable). The high cost of these instruments is due at least partially to the selectability of excitation and emission wavelengths with high spectral resolution, using diffraction gratings. Because the substrates, enzymes and dyes described above are well characterized spectrally, single-wavelength excitation sources (e.g., LEDs) may be selected along with specific filters to isolate emission and excitation wavelengths. This allows the construction of multiple low-cost detectors, so that having several samples run at the same time now becomes practical and efficient. This means that a standard reference sample of 100% DEG can be run at the same time as a test sample, using the same enzymes and under the same conditions of temperature, time, pressure and other environmental parameters. By running the two samples in parallel, the results for the test sample may be normalized, as described above, thereby removing fluctuations due to accumulated differences in enzyme activity. This measure may be reproducible through different batches of all enzyme components, and it allows contaminant concentrations to be measured more accurately than may be possible with a single detector and sample.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A device comprising:
   at least one sample cuvette space configured to contain a sample liquid;
   at least one reference cuvette space configured to contain a reference liquid;
   a first single wavelength light source constructed and arranged to illuminate at least a portion of the sample cuvette space;
   a second light source at a wavelength different from the first, the second light source constructed and arranged to illuminate at least a portion of the sample cuvette space;
   a light detector positioned to detect light transmitted from the second light source through the sample cuvette space;
   a fluorescence detector positioned to receive light emitted from the sample cuvette space at a wavelength different than that emitted from either the first or the second light source;
   a third single wavelength light source constructed and arranged to illuminate at least a portion of the reference cuvette space;
   a fourth light source at a wavelength different from the third, the fourth light source constructed and arranged to illuminate at least a portion of the reference cuvette space;
   a light detector positioned to detect light transmitted from the fourth light source through the reference cuvette space; and
   a fluorescence detector positioned to receive light emitted from the reference cuvette space at a wavelength different than that emitted from either the third or the fourth light source,
   wherein the device is constructed and arranged to measure fluorescence of at least the sample liquid and the reference liquid simultaneously.

2. The device of claim 1, wherein the device is powered by a portable battery.

3. The device of claim 1, wherein at least one of the light sources of the device is an ultraviolet light source.

4. The device of claim 1, wherein the fluorescence detector is positioned at about 90 degrees from the incoming beam.

5. The device of claim 1, wherein the device optionally further comprises a longpass filter, a shortpass filter, a bandpass filter, or a combination thereof.

* * * * *